United States Patent [19]
Davis

[11] Patent Number: 5,982,974
[45] Date of Patent: Nov. 9, 1999

[54] RELEASABLE LIGHT ADJUSTMENT MECHANISM FOR A FIBEROPTIC CONDUCTOR

[76] Inventor: James M. Davis, 4687 Pond Apple Dr. South, Naples, Fla. 33999

[21] Appl. No.: 09/182,096

[22] Filed: Oct. 27, 1998

Related U.S. Application Data

[63] Continuation-in-part of application No. 09/010,413, Jan. 21, 1998, and application No. 08/834,530, Apr. 4, 1997, Pat. No. 5,832,159, which is a continuation-in-part of application No. 08/719,839, Sep. 30, 1996, Pat. No. 5,784,510.

[51] Int. Cl.$^6$ .................... G02B 6/00; F21V 7/04
[52] U.S. Cl. ................ 385/147; 385/39; 385/901; 385/53; 362/551; 362/552; 362/583
[58] Field of Search ................... 385/115, 116, 385/147, 901, 53, 38, 39, 88; 362/551, 552, 554, 556, 583

[56] References Cited

U.S. PATENT DOCUMENTS

| | | | |
|---|---|---|---|
| 4,704,660 | 11/1987 | Robbins | 362/32 |
| 4,853,774 | 8/1989 | Danna et al. | 358/98 |
| 5,784,510 | 7/1998 | Davis | 385/53 |
| 5,802,227 | 9/1998 | Dunn et al. | 385/53 |
| 5,832,151 | 11/1998 | Riser et al. | 385/31 |
| 5,832,159 | 11/1998 | Davis | 385/53 |
| 5,838,860 | 11/1998 | Kingstone et al. | 385/100 |

*Primary Examiner*—Brian Healy
*Attorney, Agent, or Firm*—William E. Noonan

[57] ABSTRACT

A releasable light adjustment mechanism is used in combination with a fiberoptic illuminator and a fiberoptic conductor that is communicably attached to the illuminator. The conductor transmits light from the illuminator to a distal second end portion of the conductor from which the light is emitted. The adjustment mechanism includes a housing having an inlet that is communicably and releasably interengaged by the distal end portion of the conductor, an outlet and an interior passageway communicably connecting the inlet and the outlet. A color wheel or an intensity wheel is mounted rotatably in the housing and extends across the passageway. By rotating the wheel, the light transmitted through the passageway is adjusted.

8 Claims, 3 Drawing Sheets

RELEASABLE LIGHT ADJUSTMENT MECHANISM FOR A FIBEROPTIC CONDUCTOR

RELATED APPLICATIONS

This application is a continuation in part of U.S. patent application Ser. No. 09/010,413, filed Jan. 21, 1998, pending, and of U.S. patent application Ser. No. 834,530, filed Apr. 4, 1997 and issued as U.S. Pat. No. 5,832,159, which is a continuation in part of Ser. No. 719,839, filed Sep. 30, 1996 and issued as U.S. Pat. No. 5,784,510.

FIELD OF THE INVENTION

This invention relates to a releasable light adjustment mechanism for use in combination with a fiberoptic illuminator and a fiberoptic conductor that is communicably attached to the illuminator. More particularly, this invention relates to a mechanism that permits the intensity and/or color of the light transmitted through the cable to be adjusted.

BACKGROUND OF THE INVENTION

Providing adequate lighting for surgical and other medical procedures has traditionally proven to be quite difficult. In an effort to improve such lighting I have developed a number of devices including the intensity adjustable fiberoptic cable apparatuses disclosed in U.S. Pat. No. 5,784,510 and U.S. patent application Ser. No. 08/834,530 filed Apr. 4, 1997. I have also provided a fiberoptic cable apparatus with an adjustable color filter as set forth in U.S. patent application Ser. No. 09/010,413 filed Jan. 21, 1998, pending. These devices permit the surgeon or other medical personnel to quickly, conveniently, and accurately adjust the intensity and color, respectively of light used in surgery and other medical procedures. The descriptions contained in the foregoing references are incorporated in this application by reference.

SUMMARY OF INVENTION

It is an object of this invention to provide a releasable light adjustment mechanism that permits light intensity and/or color to be quickly, conveniently, and accurately adjusted by the surgeon or other person manipulating a fiberoptic light-projecting instrument.

It is a further object of this invention to provide a light adjustment mechanism that is releasably interengagable with virtually all types of fiberoptic cables and conductors and which maybe conveniently attached to and removed from the cable or other conductor as required.

Is a further object of this invention to provide a light adjustment mechanism that is conveniently attachable to and removable from a wide variety of light projecting or emitting devices.

This invention features a releasable light adjustment mechanism for use in combination with a fiberoptic illuminator and a fiberoptic conductor that is communicably attached at a first end to the illuminator. The conductor transmits light from the illuminator therethrough to a distal second end portion of the conductor from which the light is emitted. The light adjustment mechanism includes housing having an inlet that is communicably and releasably interengaged by the distal end portion of the conductor. An interior passageway communicably connects the inlet and an outlet. Means mounted in the housing extend across the passageway for adjusting the light transmitted from the inlet to the outlet through the passageway.

In a preferred embodiment, the means for adjusting may include means for controlling the intensity of light transmitted through the passageway and emitted from the outlet. The means for controlling may include an intensity wheel rotatably mounted in the housing and having a plurality of differently sized apertures formed therein. The wheel is rotatable to position a selected aperture across the interior passageway. This permits a corresponding intensity of light to be transmitted through the passageway and emitted from the outlet. The apertures may comprise a graduated series of discrete openings. Alternatively, the apertures may comprise a single generally crescent shaped opening having a continuously expanding width.

The means for adjusting may also include means for transmitting a selected wavelength band of light through the passageway. The means for transmitting may include a filter wheel mounted rotatably within the housing and carrying a plurality of light filters. Each filter transmits a selected wavelength band. The filter wheel is rotated to position a selected filter across the passageway such that a corresponding wavelength band of light is transmitted through the passageway.

The outlet may be releasably and communicably interengaged with a light emitting device.

DETAILED DESCRIPTION OF PREFERRED EMBODIMENTS

Other objects, features and advantages will occur from the following description of preferred embodiments and the accompanying drawings, in which.

Figure 1:
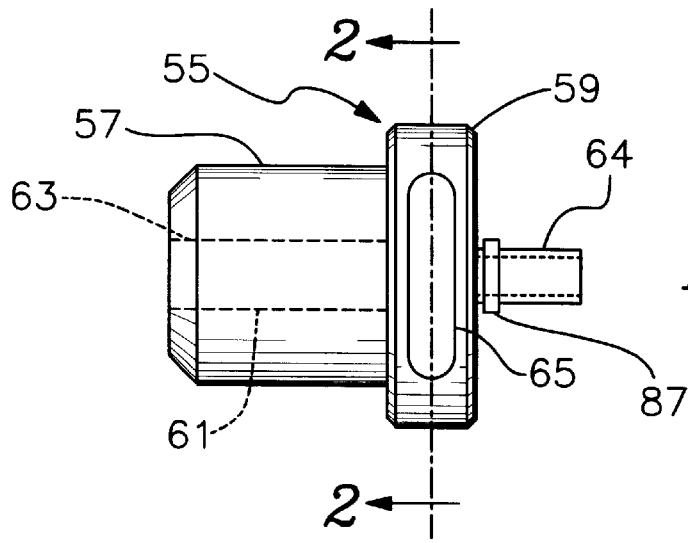
FIG. 1 is an elevational side view of a releasable light adjustment mechanism according this invention, and more particularly a mechanism used to adjust the color of the light transmitted through a fiberoptic conductor.
Figure 2:
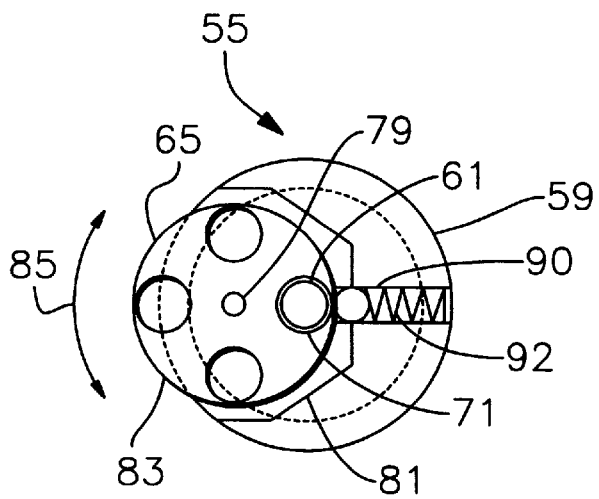
FIG. 2 is a cross sectional view of the color adjuster mechanism taken along line 2—2 of FIG 1.

There is shown in FIGS. 1 and 2 a color adjuster mechanism 55 that is releasably connectable to one end of a fiberoptic cable or other conductor. Typically, as described in Ser. No. 09/010,413, a fiberoptic cable is connected in a conventional manner to a standard illuminator and the color adjuster 55 is attached to a second distal end of the cable. Mechanism 55 includes a generally cylindrical housing 57 and an adjoining larger diameter flange 59. A central passageway 61 is formed axially through housing 57 and flange 59. A first end of passageway 61 defines an inlet 63. This inlet communicably and releasably receives the standard end plug or other connector located at the distal end of the fiberoptic cable (not shown in FIG. 1 but illustrated more clearly in connection with the second embodiment disclosed herein). Typically, the end plug of the fiberoptic cable is received in a relatively snug fit in inlet 63 of passageway 61. As a result, mechanism 55 is communicably and releasably interengaged with the fiberoptic cable.

An axial tubular element 64 is communicably joined to passageway 61. Element 64 extends from flange 59 and defines an outlet. This tubular element enables mechanism 55 to be releasably and communicably interengaged with a standard light projecting or emitting component, as is described more fully below. A resilient gasket or O-ring 87 is disposed about tubular element 64. This enables the tubular element to make a snug fit with the light-emitting component to which it is releasably interengaged.

Figure 3:
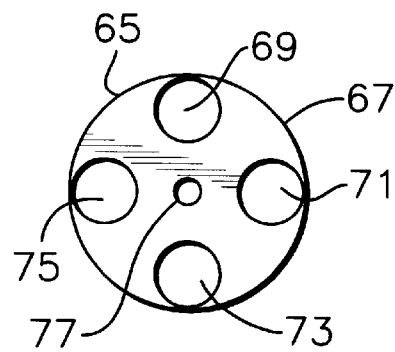
FIG. 3 is an elevational front view of the filter wheel.
Figure 4:
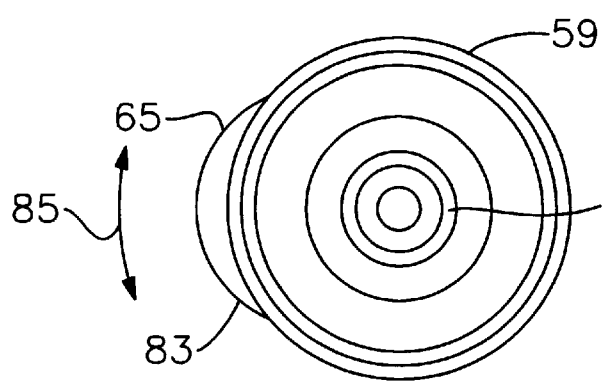
FIG. 4 is an elevational end view of the color adjuster mechanism.

A circular filter wheel 65, shown alone in FIG. 3, is rotatably mounted in flange portion 59 of adjuster housing 57. Filter wheel 65 includes a frame 67 and four individual light filters 69, 71, 73, and 75 that are mounted within frame 67. A central opening 77 is engaged by a pin 79, FIG. 2, that rotatably mounts wheel 65 within flange 59 of housing 57. As best-shown in FIG. 2, the filter wheel is received in an octagonal recess 81 formed within flange 59. Wheel 65 is axially offset within housing 57 such that a selected one of the filters 69, 71, 73, and 75 may be positioned centrally in the cylindrical housing between passageway 61 and tubular element 64. This is accomplished by rotating wheel 65 about pin 79 to position the selected filter in front of passageway 61. As best shown in FIGS. 2 and 4, a peripheral portion 83 of wheel 65 protrudes from adjuster housing flange 59. As a result, the operator can place his or her thumb against peripheral edge 83 and rotate the filter wheel 65 in the directions indicated by double-headed arrow 85. In this manner, a selected filter 69–75 may be operably positioned between passageway 61 and tubular element 64 so that only light of the corresponding color or wavelength band is transmitted through color adjuster mechanism 55.

The filter is held in place in the selected position by a locking dentent mechanism 90. This mechanism includes a spring loaded ball plunger 92 that is mounted within flange portion 59 of housing 57. A plurality of tiny recesses are formed about the circumference of wheel 65. Each recess is positioned proximate one of the filters 69, 71, 73, and 75. As the selected filter (filter 71 in FIG. 2) is rotated into position adjacent passageway 61, the ball of plunger 92 engages the recess to hold the filter wheel in that selected position. To manipulate the filter wheel into an alternative position, the operator simply presses his or her thumb against edge 83 of wheel 65 and rotates the wheel as indicated by double headed arrow 85. This urges the recess to disengage the ball of plunger 92. The plunger allows wheel 65 to rotate until the next selected filter is properly positioned in front of passageway 61. The recess associated with this filter then engages the ball plunger to provisionally lock the filter wheel and the selected filter in place within the adjuster housing.

By employing the above-described apparatus, color or wavelength bands transmitted through and emitted from cable 18 may be adjusted. Any desired number of filters may be employed in wheel 65. Typically, the filters and associated wavelength bands are selected to provide optimal illumination of various corresponding types of tissues. It should be understood that color adjuster mechanism 55 may also be located at either end of a fiberoptic cable. In certain embodiments, a pair of color adjuster mechanisms 55 may be employed with each such mechanism located proximate a respective end of the fiberoptic cable apparatus. This permits the surgeon and/or an assistant to freely and conveniently adjust the color of light being transmitted. Interruptions and distractions are avoided.

In alternative embodiments, the above described fiberoptic cable may be replaced by a light conductor composed of a transparent light transmitting material. For example, the conductor may comprise a glass or transparent plastic rod or tube. In such embodiments, a color adjustment mechanism as described above, may be communicably attached at one or both ends of the light conductor. Alternatively, the color adjustment mechanism maybe inserted at some intermediate point along the light conductor.

Additional lengths of standard fiberoptic cable or other types of light conductors may be attached to the distal end of apparatus 10. This is accomplished, for example, by simply attaching a conventional fiberoptic cable plug to tubular outlet 64 and engaging the plug with another section of standard cable. In alternative embodiments, the light emitting fitting at the distal end of apparatus 10 may include threads or other means for releasably interengaging a subsequent length of cable or conductor. In this manner, the light conductor may be constructed in any desired length and the color and intensity adjustment mechanisms may be located at desired positions that are convenient for the user.

Figure 5:
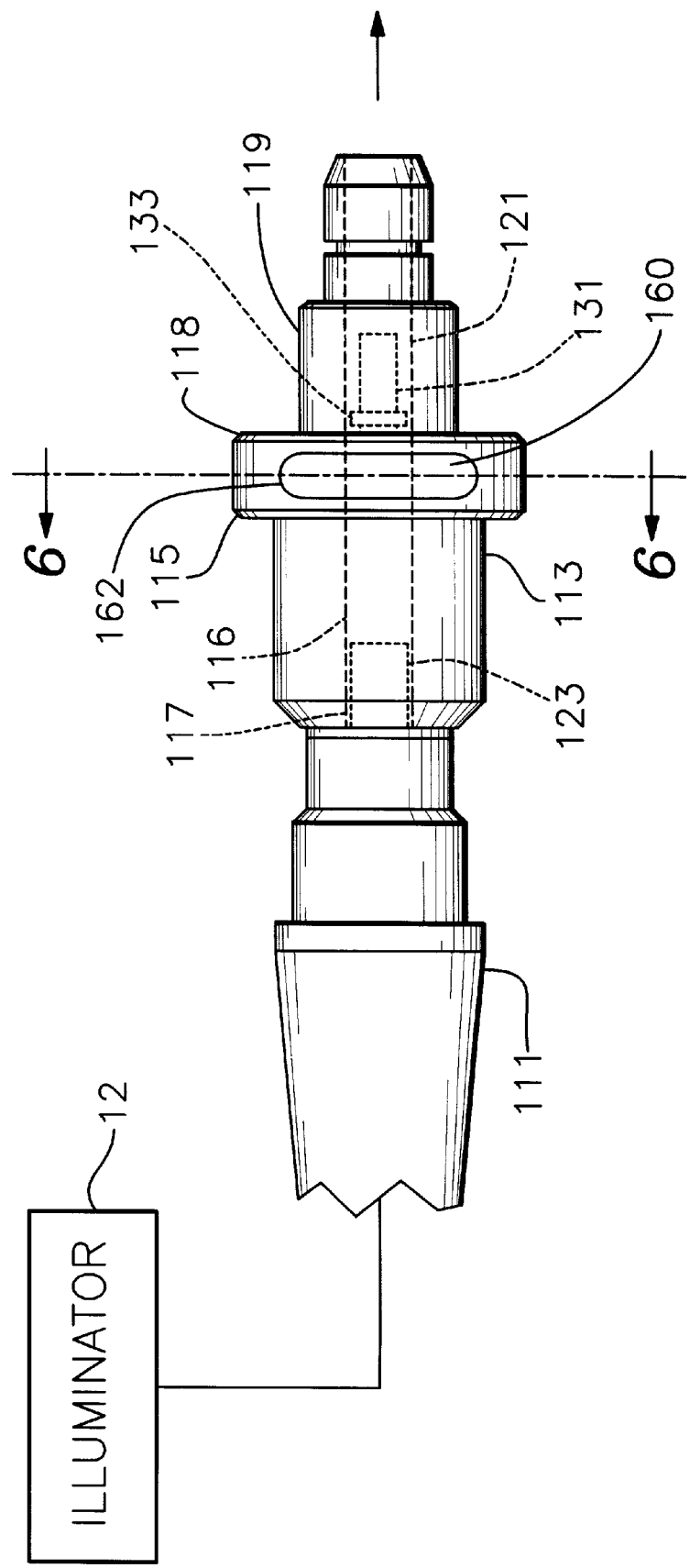
FIG. 5 is an partially schematic, elevational side view of a releasable intensity adjustment mechanism according to the invention, which mechanism is releasably interengaged between the distal end of a fiberoptic cable and a light emitting plug.

There is shown in FIG. 5 one end of a fiberoptic cable 111 that carries a releasably connected intensity controller mechanism 113. The opposite end of cable 111 is connected in a conventional manner to fiberoptic illuminator 12.

The intensity controller mechanism 113 includes a housing 115 having a central passageway 116 formed therethrough. An inlet into passageway 116 receives a standard light emitting end plug 123 of cable 111. A flange 118 is formed at a forward end of housing 115. A standard fiberoptic end plug 119 (or alternatively some other conventional light emitting component) extends from the opposite end of flange 118 and includes a central channel 121 that communicates with central passageway 116. More particularly, an elongate tubular element 131 extends axially from the leading end of the leading surface of flange 118. Element 131 communicates with passageway 116 and defines an outlet. A flange or O-ring 133 is disposed circumfertially about element 131. The tubular element is inserted into channel 121 of plug 119 and the adjustment mechanism 113 maintains a snug fit within plug 119 due to O-ring 133 interengaging the walls of channel 121.

An intensity adjustment wheel 160 is rotatably mounted within housing 115 such that the peripheral edge of the wheel protrudes through a slot 162 in flange portion 118. This is shown more clearly in FIG. 6. As illustrated therein, wheel 160 is offset relative to flange 118 and is received within a recess 164 formed in the flange. Wheel 160 is rotatably mounted by an axial pin 166 to a rearward wall 168 of flange portion 118. An analogous wall covers the forward surface of wheel 160 (i.e. the surface facing outwardly from the page in FIG. 6).

Figure 6:
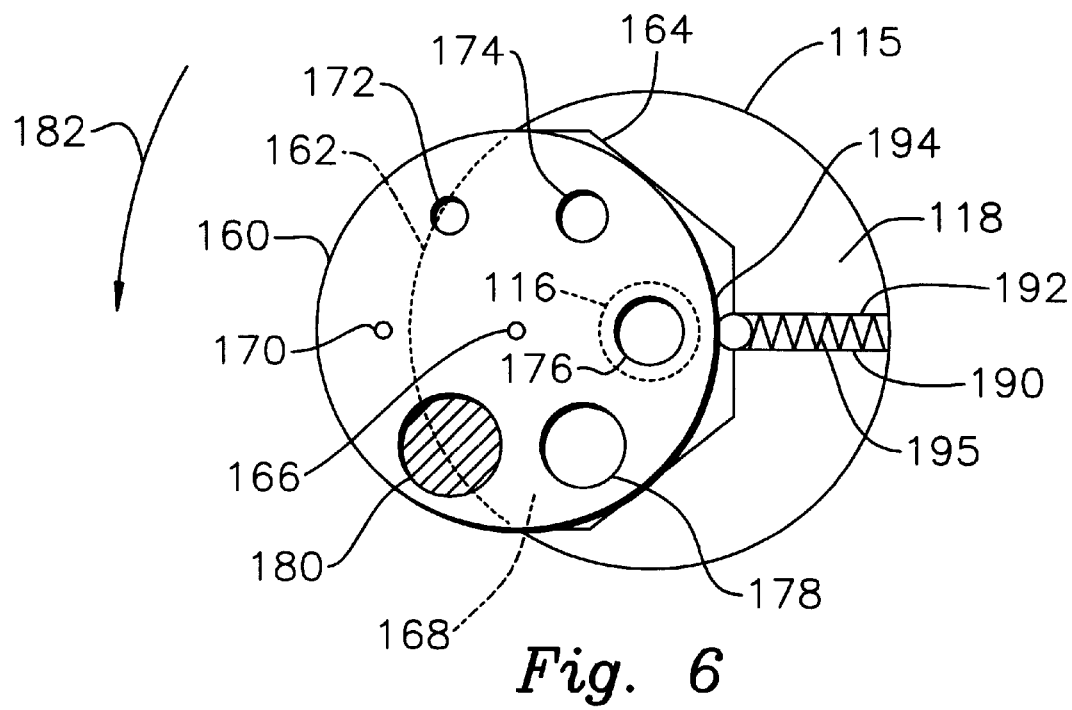
FIG. 6 is a cross sectional view taken along line 6—6 of FIG. 5.
Figure 7:
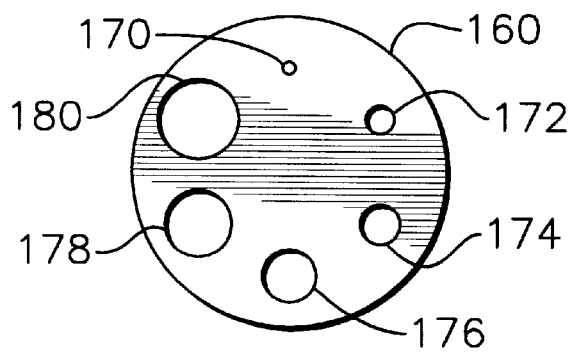
FIG. 7 is an elevational front view of an adjustable intensity wheel that employs a graduated series of openings for delivering respective levels of intensity through the cable.

As shown in FIGS. 6 and 7, intensity adjustment wheel 160 includes a graduated series of progressively larger diameter circular openings 170, 172, 174, 176, 178 and 180 that are formed at regularly spaced intervals about the wheel. These openings define a plurality of light transmitting apertures. By rotating the wheel as indicated by double headed arrow 182, openings 170–180 may be selectively positioned across passageway 116. As a result, a predetermined intensity of light (corresponding to the diameter of the selected opening) is transmitted through the passageway. If only a minimal amount of light is desired, the wheel is rotated so that smaller diameter opening 170 is positioned across passageway 116. Conversely, if a maximum amount of light is desired, large opening 180 is positioned across the passageway. Additionally, an optional infrared filter is fitted on opening 180 in FIG. 6. The remaining openings may be fully exposed or include transparent lenses. In alternative embodiments, other varieties of filters may be placed in one or more of the openings.

Each opening in wheel 160 is held in place across passageway 116 by a releasable locking mechanism 190. In particular, flange portion 118 includes a radial slot 192 that houses a bearing 194. The bearing is urged inwardly toward the center of flange portion 118 and into recess 164 by a spring mechanism 195. A plurality of indents or recesses, not shown, are formed about the periphery of wheel 160. Each such indent is positioned on the periphery of wheel 160 adjacent to a respective one of the openings 170–180. When a particular opening, e.g. opening 176, is positioned across passageway 116, spring mechanism 195 urges bearing 194 to engage the corresponding adjacent indent formed in the periphery of wheel 160. This constrains the wheel so that the opening is held in position across passageway 116. Unintended movement of the selected filter is prevented. To adjust the intensity, the operator simply places his or her thumb against the peripheral portion of the wheel that protrudes from housing 114. The wheel is then rotated as indicated by double-headed arrow 182. Bearing 194 disengages the notch in which is has previously resided and compresses spring mechanism 195. As a result, the wheel is released and free to rotate. The operator turns the wheel until a new selected opening is placed in position across the passageway. The spring and bearing mechanism re-engage with the notch corresponding to the opening. As a result, the wheel is again held in place until subsequent adjustment is desired.

Figure 8:
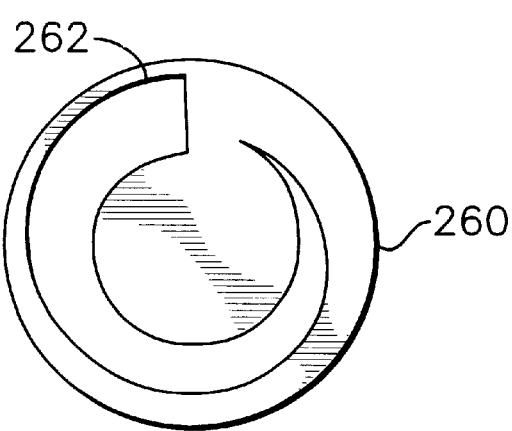
FIG. 8 is a front elevational view of an alternative intensity adjustment wheel that employs a single variable width opening.

An alternative intensity adjustment wheel 260 is depicted in FIG. 8. That wheel is mounted in a housing in a manner analogous to wheel 160 shown in FIGS. 6 and 7. Wheel 260 is similarly provided with a plurality of differently sized, light transmitting apertures. In this version the apertures are defined by a single, generally crescent-shaped opening 262. Opening 262 features a continuously expanding width. By rotating wheel 260 in the manner previously described for wheel 160, a selected portion of opening 262 is positioned across the passageway formed through the intensity adjustment mechanism. This portion of the opening forms an aperture of a selected width. As a result, a desired intensity of light is transmitted from the fiberoptic cable to the light projecting end plug 119, FIG. 5.

A second light controlling mechanism, analogous to mechanism 113 shown in FIG. 14, is releasably employed at the opposite end of fiberoptic cable 111. As in the previously described embodiment, this permits the operator to adjust the intensity of light directed to the cable at either the end of the cable that is plugged into the illuminator or at the opposite, distal end.

Significant advantages are achieved by locating an intensity controller and/or color adjuster at the distal end of the cable apparatus. Most significantly, this apparatus permits the fiberoptic cable intensity and color adjustments to be performed independently of the illuminator and at the distal end of the cable by the surgeon or other person handling the fiberoptic cable. This user can adjust the intensity instantaneously and/or color and without having to divert his or her attention from the task at hand. Likewise, the intensity adjustments can be made without requiring the assistance of additional personnel to control the intensity at the illuminator. Such personnel are thereby free to perform other needed tasks. The ability for the doctor or other person using the cable to personally perform the lighting adjustments also eliminates extraneous communications between that person and assisting personnel and eliminates the possibility of miscommunications. Lighting adjustments are accomplished far more effectively, quickly and efficiently than has been possible using conventional fiberoptic illuminators.

It should be further understood that the color adjustment mechanism may be utilized either with or without intensity adjustment mechanisms and vice versa. Various numbers of light adjusters may be employed. Assorted means of releasably interconnecting the light adjustment components to the fiberoptic cable apparatus and to one another may also be utilized. For example, the versions disclosed herein employ plug type connections. See FIGS. 1 & 5. In alternative embodiments, threaded means for interconnecting the cable and the light adjuster may be used. See U.S. Pat. No. 5,784,510. Such constructions will be understood to those skilled in the art. Color adjuster mechanism 55 may be positioned along fiberoptic cable 18 at any convenient location, although it is preferably that it be placed proximate one or both of the ends of the cable. Although circular intensity and filter wheels are disclosed herein, in alternative embodiments, the wheels may employ other non-circular shapes.

It should be understood that, although the embodiments shown herein employ lighting adjustment mechanisms at a distal end of the fiberoptic cable, in alternative embodiments the light controllers may be located between the illuminator and the cable or between two sections of cable or other light conductor. Releasability of the lighting adjuster from the cable permits the adjuster to be conventionally positioned along and adapted to the conductor as required for the particular medical procedure involved.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. A releasable light adjustment mechanism for use in combination with a fiberoptic illuminator and a fiberoptic conductor that is communicably attached at a first end to the illuminator, said conductor transmitting light from the illuminator therethrough to a distal second end portion of the conductor from which the light is emitted, said mechanism comprising:

an adjuster housing that is releasably and communicably connected to the second end portion of the conductor and being separate, distinct and remote from the fiberoptic illuminator, said adjuster housing having an inlet that is communicably and releasably interengaged by the distal light-emitting second end portion of the conductor, an outlet separate and distinct from said inlet and an interior passageway communicably connecting said inlet and said outlet; and means mounted in said housing and extending across said passageway for adjusting the light transmitted from said inlet to said outlet through said passageway of said adjuster housing.

2. The mechanism of claim 1 in which said means for adjusting include means for controlling the intensity of light transmitted through said passageway and emitted from said outlet.

3. The mechanism of claim 2 in which said means for controlling include an intensity wheel rotatably mounted in said housing and having a plurality of differently sized apertures formed therein, said wheel being rotatable to position a selected aperture across said interior passageway to permit a corresponding intensity of light to be transmitted through said passageway and emitted from said outlet.

4. The mechanism of claim 3 in which said apertures comprise a graduated series of discrete openings.

5. The mechanism of claim 3 in which said apertures comprise a single generally crescent shaped opening having a continuously expanding width.

6. The mechanism of claim 1 in which said means for adjusting include means for transmitting a selected wavelength band of light through said passageway.

7. The mechanism of claim 6 in which said means for transmitting includes a filter wheel mounted rotatably within said housing and carrying a plurality of light filters, each filter transmitting a selected wavelength band, said filter wheel being rotated to position a selected filter across said passageway such that a corresponding wavelength band of light is transmitted through said passageway.

8. The mechanism of claim 1 in which said outlet is releasably and communicably interengagable with a light emitting device.

* * * * *